United States Patent
Simpson et al.

(10) Patent No.: US 11,896,273 B2
(45) Date of Patent: Feb. 13, 2024

(54) ORTHOGNATHIC SURGICAL IMPLANT ASSEMBLY HAVING PRE-OSTEOTOMY AND POST-OSTEOTOMY ALIGNMENT MEMBERS

(71) Applicants: Travis Simpson, Jacksonville, FL (US); Tirth Patel, Jacksonville, FL (US)

(72) Inventors: Travis Simpson, Jacksonville, FL (US); Tirth Patel, Jacksonville, FL (US)

(73) Assignee: KLS MARTIN, L.P., Jacksonville, FL (US)

( * ) Notice: Subject to any disclaimer, the term of this patent is extended or adjusted under 35 U.S.C. 154(b) by 437 days.

(21) Appl. No.: 17/082,908

(22) Filed: Oct. 28, 2020

(65) Prior Publication Data
US 2021/0121215 A1    Apr. 29, 2021

Related U.S. Application Data

(60) Provisional application No. 62/926,965, filed on Oct. 28, 2019.

(51) Int. Cl.
| | | |
|---|---|---|
| *A61B 17/80* | (2006.01) | |
| *A61B 17/17* | (2006.01) | |
| *A61B 34/10* | (2016.01) | |
| *A61B 17/56* | (2006.01) | |

(52) U.S. Cl.
CPC ........ *A61B 17/8071* (2013.01); *A61B 17/176* (2013.01); *A61B 17/8052* (2013.01); *A61B 34/10* (2016.02); *A61B 2017/564* (2013.01); *A61B 2034/102* (2016.02); *A61B 2034/105* (2016.02)

(58) Field of Classification Search
CPC .................. A61B 17/8071; A61B 17/176
See application file for complete search history.

(56) References Cited

U.S. PATENT DOCUMENTS

| | | | |
|---|---|---|---|
| 9,066,733 B2 | 6/2015 | Furrer et al. | |
| 9,277,948 B2 | 3/2016 | Furrer et al. | |
| 9,855,056 B2 | 1/2018 | Furrer et al. | |
| 10,470,806 B2 | 11/2019 | Kohler et al. | |
| 2019/0038414 A1* | 2/2019 | Johnston, Jr. | ......... A61F 2/2875 |

OTHER PUBLICATIONS

PCT International Search Report and Written Opinion, PCT/US2020/057747, International Filing Date Oct. 28, 2020, dated Jan. 14, 2021, 12 pages.
Copenheaver, ISA/US, PCT International Search Report and Written Opinion of the International Searching Authority, dated Jan. 14, 2021, PCT/US2020/057747.

* cited by examiner

*Primary Examiner* — Olivia C Chang
(74) *Attorney, Agent, or Firm* — Thomas C. Saitta

(57) ABSTRACT

An implant assembly and its method of use, used in computer-aided orthognathic surgery for properly repositioning a mobile bone segment separated by osteotomy from a malformed mandible, maxilla or chin, the implant assembly comprising fixation bone plates, at least one removable alignment plate for proper pre-osteotomy placement of the implant assembly onto the mandible, maxilla or chin, at least one removable post-osteotomy alignment plate for proper positioning of the mobile bone segment relative to the mandible, maxilla or chin, and a removable cutting guide for guiding the osteotomy saw during separation of the mobile bone segment from the mandible, maxilla or chin.

11 Claims, 6 Drawing Sheets

ORTHOGNATHIC SURGICAL IMPLANT ASSEMBLY HAVING PRE-OSTEOTOMY AND POST-OSTEOTOMY ALIGNMENT MEMBERS

BACKGROUND OF THE INVENTION

This invention relates generally to bone fixation plates or implants and cutting guides used in computer-aided orthognathic surgery and related methods of designing, creating and using such devices, and more particularly relates to such devices and methods that are patient-specific such that the plates or implants are customized to match the particular patient.

Orthognathic surgery is surgery designed to correct conditions of the jaw and face related to structure, growth, sleep apnea, TMJ disorders, malocclusion problems owing to skeletal disharmonies, or other orthodontic problems that cannot be easily treated with braces. Typically during such surgery, bone is cut to create non-mobile or base bone segment(s) and mobile or separated bone segment(s), and the mobile bone segment(s) are repositioned and realigned to correct a dentofacial or similar deformity, with bone plates or implants used to fix the detached or mobile bone segments to the non-mobile bone segments in the desired post-osteotomy orientation. The word "osteotomy" means the division or excision of bone. The osteotomies may be performed on the maxilla (e.g., a LeFort I), the mandible (e.g., a sagittal split), or the chin (e.g., a genioplasty).

Early techniques utilized stock bone fixation plates that had to be manipulated (i.e., cut or bent) by the surgeon in order to provide a better fit onto the bone surface topography. Such techniques resulted at best in approximations to the bone surface topography.

Modern orthognathic surgery makes use of computer-aided design and manufacturing techniques whereby surgeons and technicians create pre-osteotomy and post-osteotomy virtual 3-D models of a patient's bone structure topography. The virtual pre-osteotomy 3-D model is produced using various electronic scanning techniques and shows the current configuration of the bone structure before corrective surgery. The surgeon along with technicians then virtually manipulates the pre-osteotomy model to produce the desired post-osteotomy configuration and orientation for the corrected bone structure. One or more virtual guides for cutting the osteotomy or marking the location of the osteotomy on the maxilla, mandible or chin, as well as for drilling holes to receive bone fastening screws, are created within the computer system, and actual guides are then manufactured based on the specifications of the virtual guides. Likewise, one or more virtual fixation bone plates are then configured and actual fixation bone plates are produced from the specifications, such that when the actual fixation bone plates are attached to the non-mobile bone segment and the re-positioned mobile or detached bone segment after the osteotomy, the bone segments will be properly positioned relative to each other in the desired post-osteotomy configuration.

The guide is designed to conform to the pre-osteotomy surface topography or configuration of the patient's bone structure, the inner surface of the guide matching the surface topography such that the surgeon can easily position the guide in the proper location. The surgeon then uses the guide to mark the location for the osteotomy and either marks or drills holes through apertures in the guides, the holes being properly positioned to receive the bone screws used to fasten the fixation implants to the bone segments with the bone segments positioned in the desired post osteotomy relationship. Alternatively, rather than using the guide for marking purposes, the guide may be produced with physical structures to guide the osteotomy saw during the severing of the bone. The fixation bone plates are produced such that a first portion of the plate conforms to the surface topography of the non-mobile bone segment and a second portion of the plate conforms to the surface topography of the mobile bone section. A transition portion connects the first and second conforming portions, such that the positioning and orientation of the second conforming portion results in proper relocation and orientation of the mobile bone segment.

While this computer-aided orthognathic surgery method and devices is an improvement over the earlier techniques and devices, proper location of the fixation bone plates is still problematic, since it is most desirable to minimize the footprint or contact surface areas of the fixation bone plates. In many instances the contact surface areas of the fixation bone plates is only slightly greater than the diameter of the bone screw apertures.

It is an object of this invention to an improved, patient-specific, orthognathic surgical implant assembly and method of use that addresses this problem by providing such assembly with an increased amount of contact surface areas so that proper location of the guide and bone plates is more easily achieved. It is an object of this invention to provide such an improved orthognathic surgical implant assembly with the assembly having one or more removable pre-osteotomy alignment plate members for proper pre-osteotomy positioning of the fixation bone plate(s) on the non-mobile or base bone segment and one or more removable post-osteotomy alignment plate members for proper post-osteotomy positioning of the fixation bone plate(s) on the mobile or detached bone segment(s), as well as the method of use of such an implant assembly. It is a further object to provide in some embodiments such an implant assembly with a cutting guide for marking or performing the osteotomy.

After the computer-aided design steps have been accomplished and the implant assembly has been manufactured, the patient-specific implant assembly is created such that one or more pre-osteotomy conforming conforming alignment plates and one or more post-osteotomy conforming conforming alignment plates are rigidly connected to the one or more fixation bone plates by bridging members that are sized and configured to be easily severed after implantation of the one or more fixation bone plates onto the bone tissue. The implant assembly is positioned on the patient by properly orienting the pre-osteotomy conforming conforming alignment plates and the pre-osteotomy conforming portions of the one or more fixation bone plates onto the non-mobile bone segment, affixing the pre-osteotomy conforming portions of the one or more fixation bone plates onto the non-mobile bone segment using mechanical fasteners such as bone screws, removing the pre-osteotomy conforming alignment plates from the implant assembly, cutting the osteotomy to create the mobile bone segment, orienting and positioning the mobile bone segment to the one or more post-osteotomy conforming alignment plates and the post-osteotomy conforming portions of the one or more fixation bone plates, affixing the mobile bone segment to the post-osteotomy conforming portions of the one or more fixation bone plates using mechanical fasteners such as bone screws, and removing the post-osteotomy conforming alignment plates from the implant assembly.

SUMMARY OF THE INVENTION

In brief summary, the invention in general is a patient-specific, customized, implant assembly used in computer-aided orthognathic surgery for properly repositioning a mobile bone segment detached by osteotomy from a non-mobile or base bone segment, such as a mandible, maxilla or chin, as well as the method of designing, using and implanting the implant assembly. The implant assembly comprises one or more fixation bone plates or implants having a pre-osteotomy conforming portion, a transition portion and a post-osteotomy conforming portion, one or more removable pre-osteotomy alignment plate members for proper pre-osteotomy placement and affixation of the pre-osteotomy conforming portions of the fixation bone plates onto the non-mobile bone segment, one or more removable post-osteotomy alignment plate members for proper positioning and affixation of the mobile bone segment onto the post-osteotomy conforming portions of the fixation bone plates, and preferably a cutting guide for marking the location of the osteotomy on the mandible, maxilla or chin or for guiding the osteotomy saw during separation of the mobile bone segment from the non-mobile bone segment. The one or more fixation bone plates, one or more removable pre-osteotomy conforming alignment plates, one or more removable post-osteotomy conforming alignment plates and cutting guide are connected by bridging members to form a rigid implant assembly, the bridging members being of reduced dimension and configuration so as to be easily severed after the implant assembly has been affixed to the bone tissue to remove the one or more removable pre-osteotomy conforming alignment plates, one or more removable post-osteotomy conforming alignment plates and cutting guide from the one or more fixation bone plates.

The size, shape and conformation of the rigid implant assembly is determined by 3-D computer-aided design and modelling in known manner, whereby a virtual 3-D model of the pre-osteotomy bone structure of a patient is first produced using scanning techniques. A surgeon and/or technician determines the best location of an osteotomy and the proper repositioning of a mobile bone segment to be detached from a non-mobile segment of the bone structure and creates a virtual 3-D post-osteotomy model of the desired post-operative morphology. Based on the virtual 3-D models, the proper size, shape and conformation of the pre-osteotomy conforming portion of each fixation bone plate that mounts to the non-mobile bone segment is determined, along with the proper location for screw-receiving apertures. Likewise, the proper size, shape and conformation of the post-osteotomy conforming portion of each fixation bone plate that mounts to the mobile bone segment is determined, along with the proper location for screw-receiving apertures. Furthermore, the proper size, shape and conformation of each removable pre-osteotomy alignment plate that conforms to the non-mobile bone segment is determined, and the proper size, shape and conformation of each removable post-osteotomy alignment plate that conforms to the mobile bone segment is determined. The pre-osteotomy and post-osteotomy conforming alignment plates are connected to the one or more fixation bone plates by bridging members which are sized and configured to be easily severed. If present, the position of the cutting guide is also determined, and the cutting guide being likewise connected to the fixation bone plates by bridging members that are easily severed. The actual implant assembly is then manufactured based on the design specifications.

The orthognathic procedure is accomplished by properly orienting the one or more pre-osteotomy conforming alignment plates onto the non-mobile or base bone segment and then affixing the pre-osteotomy conforming portion of each of the one or more fixation bone plates to the non-mobile bone segment using bone screws or similar mechanical fasteners, the one or more removable pre-osteotomy conforming alignment plates in combination with the pre-osteotomy conforming portions of the fixation bone plates insuring that the one or more fixation bone plates are properly located on the non-mobile bone segment. The one or more removable pre-osteotomy conforming alignment plates are then separated from the pre-osteotomy portion of the fixation bone plates by severing the bridging members. The cutting guide if present is then used to mark or perform the osteotomy, creating a detached mobile bone segment from the non-mobile bone segment. The mobile bone segment is then affixed to the post-osteotomy conforming portion of the one or more fixation bone plates with bone screws or similar mechanical fasteners, the one or more removable post-osteotomy conforming alignment plates in combination with the post-osteotomy conforming portions of the fixation bone plates insuring that the post-osteotomy conforming portion is properly located on the mobile bone segment, which insures that the mobile bone segment is properly oriented and located relative to the non-mobile bone segment in a fixed, rigid manner. The one or more removable post-osteotomy conforming alignment plates are then separated from the post-osteotomy conforming portion of the one or more fixation bone implant. The size, shape and configuration of the transition portion of each fixation bone plate results in proper re-positioning of the mobile bone segment relative to the non-mobile bone segment, such that upon bone regeneration the combined mobile and non-mobile bone segments produce a bone structure having the desired configuration and morphology.

In alternative summary, the invention is a customized, patient-specific implant assembly comprising: one or more fixation bone plates each comprising a pre-osteotomy conforming portion and a post-osteotomy conforming portion joined by a transition portion; bone screw apertures disposed in the pre-osteotomy conforming portions and the post-osteotomy conforming portions of the one or more fixation bone plates; and one or more removable pre-osteotomy conforming alignment plates and one or more post-osteotomy conforming alignment plates connected to the one or more fixation bone plates by bridging members. Furthermore, such implant assembly further comprising a removable cutting guide connected to the one or more fixation bone plates; wherein the pre-osteotomy conforming portion and a post-osteotomy conforming portion of each of the one or more fixation bone plates comprises a surface contact area, and wherein the one or more removable pre-osteotomy conforming alignment plates and one or more post-osteotomy conforming alignment plates each comprise a contact surface area greater than the contact surface area of the pre-osteotomy conforming portion and a post-osteotomy conforming portion of each of the one or more fixation bone plates; wherein the one or more removable pre-osteotomy conforming alignment plates and one or more post-osteotomy conforming alignment plates are non-planar; and/or wherein the one or more removable pre-osteotomy conforming alignment plates and one or more post-osteotomy conforming alignment plates are non-planar.

Alternatively, the invention is a customized, patient-specific implant assembly configured to fixedly position a mobile bone segment relative to a non-mobile bone segment, the mobile and non-mobile bone segments having surface topographies, the implant assembly comprising: one or more fixation bone plates each comprising a pre-osteotomy conforming portion and a post-osteotomy conforming portion joined by a transition portion, wherein the pre-osteotomy conforming portion is configured to conform to a portion of the surface topography of the non-mobile bone segment, and wherein the post-osteotomy conforming portion is configured to correspond to a portion of the surface topography of the mobile bone segment; bone screw apertures disposed in the pre-osteotomy conforming portions and the post-osteotomy conforming portions of the one or more fixation bone plates; and one or more removable pre-osteotomy conforming alignment plates and one or more post-osteotomy conforming alignment plates connected to the one or more fixation bone plates by bridging members, wherein the one or more removable pre-osteotomy conforming alignment plates are configured to conform to other portions of the surface topography of the non-mobile bone segment, and wherein the one or more removable post-osteotomy conforming alignment plates are configured to conform to other portions of the surface topography of the mobile bone segment. Furthermore, such an implant assembly further comprising a removable cutting guide connected to the one or more fixation bone plates; and/or wherein the pre-osteotomy conforming portion and a post-osteotomy conforming portion of each of the one or more fixation bone plates comprises a surface contact area, and wherein the one or more removable pre-osteotomy conforming alignment plates and one or more post-osteotomy conforming alignment plates each comprise a contact surface area greater than the contact surface area of the pre-osteotomy conforming portion and a post-osteotomy conforming portion of each of the one or more fixation bone plates.

Alternatively, a method of performing orthognathic surgery comprising the steps of: creating a virtual 3-D model of a bone having a surface topography; creating a virtual 3-D model of the bone wherein the bone is virtually severed to create a virtual mobile bone segment and a virtual non-mobile bone segment; moving the virtual bone segment relative to the non-mobile bone segment; creating a virtual implant assembly comprising one or more fixation bone plates each comprising a pre-osteotomy conforming portion and a post-osteotomy conforming portion joined by a transition portion; bone screw apertures disposed in the pre-osteotomy conforming portions and the post-osteotomy conforming portions of the one or more fixation bone plates; and one or more removable pre-osteotomy conforming alignment plates and one or more post-osteotomy conforming alignment plates connected to the one or more fixation bone plates by bridging members; creating an actual implant assembly matching the virtual implant assembly, the actual implant assembly comprising one or more fixation bone plates each comprising a pre-osteotomy conforming portion and a post-osteotomy conforming portion joined by a transition portion; bone screw apertures disposed in the pre-osteotomy conforming portions and the post-osteotomy conforming portions of the one or more fixation bone plates; and one or more removable pre-osteotomy conforming alignment plates and one or more post-osteotomy conforming alignment plates connected to the one or more fixation bone plates by bridging members; positioning the actual implant assembly on the bone and such that the pre-osteotomy conforming portions of the one or more fixation bone plates and the one or more pre-osteotomy conforming alignment plates conform to the surface topography of the bone; affixing the pre-osteotomy conforming portions of the one or more fixation bone plates to the bone with mechanical fasteners; removing the one or more pre-osteotomy conforming alignment plates from the implant assembly; performing an osteotomy to divide the bone into a mobile bone segment and a non-mobile bone segment; positioning the mobile bone segment such that the post-osteotomy conforming portions of the one or more fixation bone plates and the one or more post-osteotomy conforming alignment plates conform to the surface topography of the mobile bone segment; affixing the post-osteotomy conforming portions of the one or more fixation bone plates to the bone with mechanical fasteners; and removing the one or more post-osteotomy conforming alignment plates from the implant assembly. Furthermore, the method wherein the step of creating a virtual implant assembly further comprises creating a cutting guide joined to the one or more fixation bone plates; and wherein the step of creating an actual implant assembly further comprises creating a cutting guide joined to the one or more fixation bone plates; and further comprising the step of removing the cutting guide after the step of performing an osteotomy.

DETAILED DESCRIPTION OF THE INVENTION

It is to be understood that the drawings are presented for illustrative, enabling and descriptive purposes. The drawings present a representative embodiment of the invention and are not intended to be limiting as to the scope and definition of the invention. As used herein, the term "implant assembly" defines the combination of multiple components formed as an integral, rigid, one-piece member, wherein the components are separable from each other at different stages of the surgical procedure. The implant assembly 10 is a customized, patient-specific device having conforming surfaces that correspond and match the adjacent surface topography of the bone or tissue when the implant assembly 10 is properly positioned on the patient. The implant assembly 10 is useful in differing orthognathic procedures, such as correction of mandible deformity, wherein the anterior segment of the mandible is separated from and repositioned relative to the posterior segments of the mandible, or correction of a chin deformity, wherein the anterior segment of the chin is separated from and repositioned relative to the posterior segment of the chin, and/or correction of a maxilla deformity, wherein the anterior segment of the maxilla is separated from and repositioned relative to the posterior segment of the maxilla. For ease of illustration and discussion, the invention will be described in both general terms and in terms of a representative embodiment involving correction of a maxilla deformity.

Figure 1:
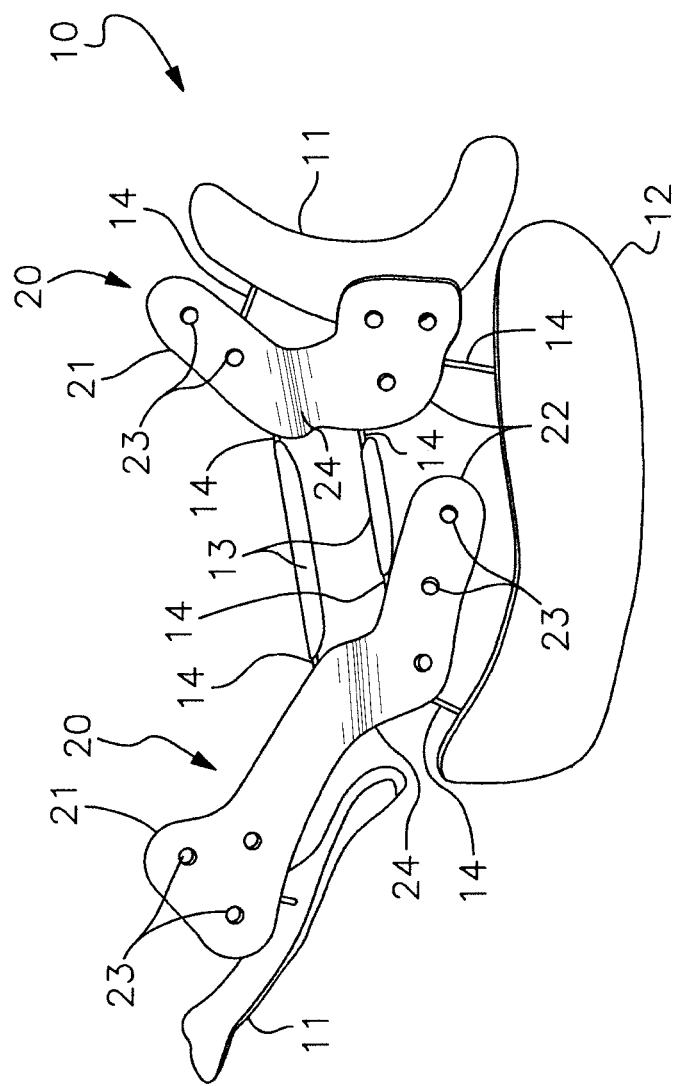
FIG. 1 illustrates a representative embodiment of the implant assembly used in orthognathic repositioning of a maxilla, the embodiment having a pair of fixation bone plates, a pair of pre-osteotomy alignment members and a single post-osteotomy alignment member. A companion implant assembly configured for the opposite side of the maxilla is not shown.

The invention in general is a patient-specific, customized, implant assembly 10, as shown in FIG. 1, used in computer-aided orthognathic surgery for properly repositioning a mobile bone segment 32 detached by osteotomy from a non-mobile or base bone segment 31, such as a mandible, maxilla or chin, as well as the method of designing, using and implanting the implant assembly 10. The implant assembly 10 comprises one or more fixation bone plates or implants 20 having a pre-osteotomy conforming portion 21, a transition portion 24 and a post-osteotomy conforming portion 22, one or more removable pre-osteotomy alignment plate members 11 for proper pre-osteotomy placement and affixation of the pre-osteotomy conforming portions 21 of the fixation bone plates 20 onto the non-mobile bone segment 31, one or more removable post-osteotomy alignment plate members 12 for proper positioning and affixation of the mobile bone segment 32 onto the post-osteotomy conforming portions 22 of the fixation bone plates 20, and preferably a cutting guide member 13 for marking the location of the osteotomy 33 on the mandible, maxilla or chin or for guiding the osteotomy saw during separation of the mobile bone segment 32 from the non-mobile bone segment 31. The one or more fixation bone plates 20, one or more removable pre-osteotomy conforming alignment plates 11, one or more removable post-osteotomy conforming alignment plates 12 and cutting guide 13 are connected by bridging members 14 to form a rigid implant assembly, the bridging members 14 being of reduced dimension and configuration so as to be easily severed after the implant assembly 10 has been affixed to the bone tissue to remove the one or more removable pre-osteotomy conforming alignment plates 11, one or more removable post-osteotomy conforming alignment plates 12 and cutting guide 13 from the one or more fixation bone plates 20.

The pre-osteotomy conforming conforming alignment plates 11 and the post-osteotomy conforming conforming alignment plates 12 provide a generous surface contact area on their interior surfaces, the plates having length and width dimensions significantly greater than their thickness dimension (i.e., the term "plate" is used in its standard definitional sense, and precludes bars or rods wherein the width dimension is substantially equal to the thickness dimension). Most preferably, the contact surface area of the pre-osteotomy conforming conforming alignment plates 11 and the post-osteotomy conforming conforming alignment plates 12 is greater than the contact surface area of the pre-osteotomy conforming portions 21 and post-osteotomy conforming portions 22 of the fixation bone plates 20. The interior contact surfaces of the pre-osteotomy conforming conforming alignment plates 11 and the post-osteotomy conforming conforming alignment plates 12 correspond or match the surface topography of the bone segments 31 or 32 over the area of contact, as determined and produced using computer-aided design and manufacture. The pre-osteotomy conforming conforming alignment plates 11 and the post-osteotomy conforming conforming alignment plates 12 are non-planar and may be formed with valleys or pockets to receive edges of bone segments 31 or 32.

Figure 3:
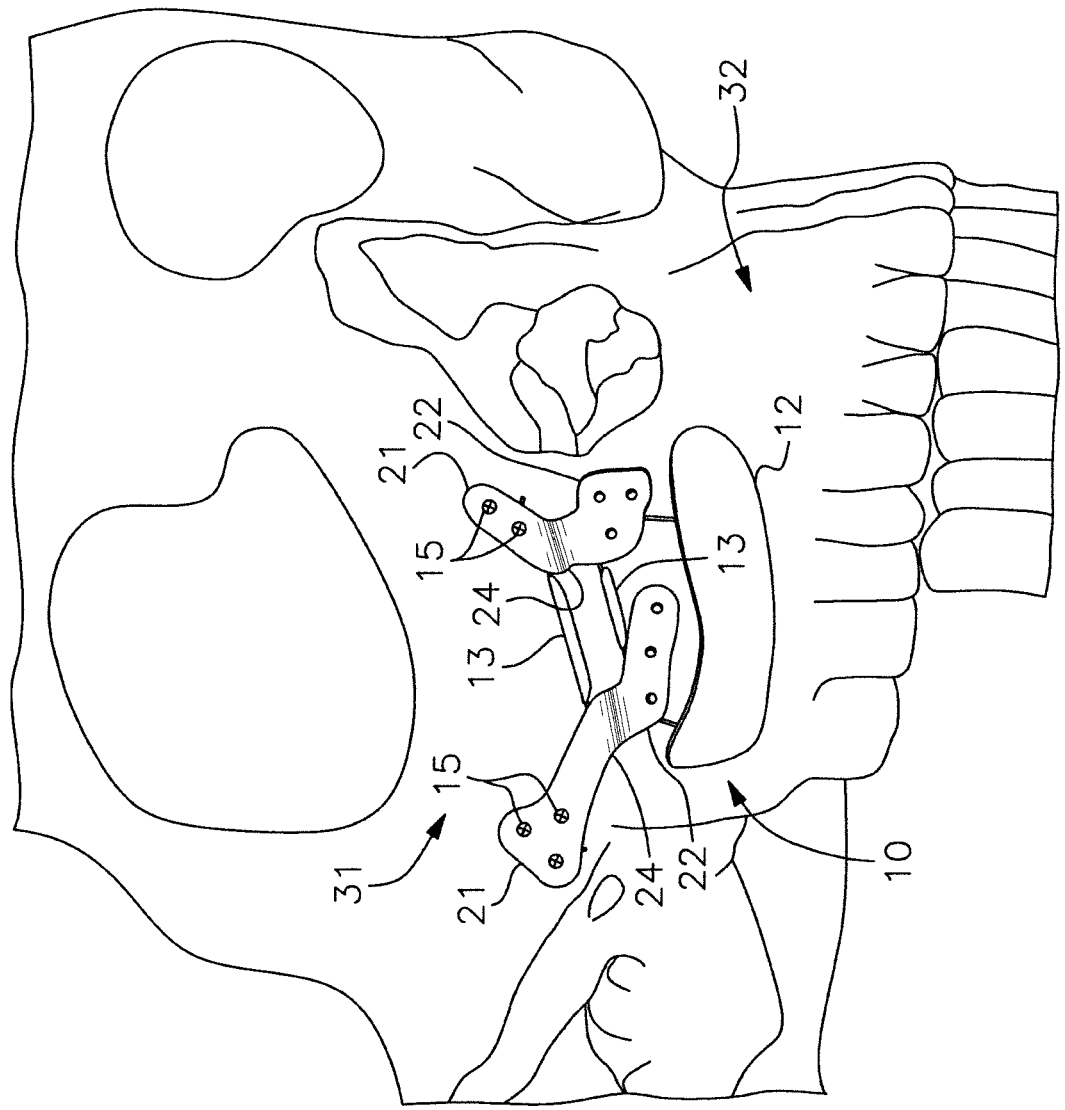
FIG. 3 illustrates the implant assembly having the pre-osteotomy conforming portion affixed to the maxilla by bone screws and the pre-osteotomy alignment members removed from the assembly.

The fixation bone plates 20 comprise a pre-osteotomy conforming portion 21 and a post-osteotomy conforming portion 22, each having interior contact surfaces that correspond or match the surface topography of the bone segments 31 or 32 over the area of contact, as determined and produced using computer-aided design and manufacture. The pre-osteotomy conforming portion 21 and a post-osteotomy conforming portion 22 are rigidly joined by a transition portion 24, configured and produced using computer-aided design and manufacture, such that with the pre-osteotomy conforming portion 21 affixed to the non-mobile bone segment 31 with bone screws or similar mechanical fasteners 15 inserted through screw apertures 23, the desired position and orientation of the post-osteotomy conforming portion 22 is attained, as shown in FIG. 3.

The cutting guide 13 comprises one or two elongated bodies spaced to define a gap through which an osteotomy saw may be inserted and guided to create the osteotomy 33. The cutting guide 13 may or may not be formed as a conforming member assisting in proper positioning of the implant assembly 10 on the non-mobile bone segment 31.

The implant assembly 10 is a rigid construct, wherein the one or more fixation bone plates 20, one or more removable pre-osteotomy conforming alignment plates 11, one or more removable post-osteotomy conforming alignment plates 12 and cutting guide 13 are connected by bridging members 14 to form a rigid implant assembly, the bridging members 14 being of reduced dimension and configuration so as to be easily severed after the implant assembly 10 has been affixed to the bone tissue to remove the one or more removable pre-osteotomy conforming alignment plates 11, one or more removable post-osteotomy conforming alignment plates 12 and cutting guide 13 from the one or more fixation bone plates 20. The bridging members 13 are most preferably designed and formed in the shape of elongated rods or bars of relatively thin dimension such that they are easily severed by cutting implements, and may be provided with reduced diameter necks adjacent the joined components.

The size, shape and conformation of the rigid implant assembly 10 is determined by 3-D computer-aided design and modelling in known manner, whereby a virtual 3-D model of the pre-operative bone structure of a patient is first produced using scanning techniques. A surgeon and/or technician determines the best location of an osteotomy 33 and the proper repositioning of a mobile bone segment 32 to be detached from a non-mobile segment 31 of the bone structure and creates a virtual 3-D post-osteotomy model of the desired post-operative morphology. Based on the virtual 3-D models, the proper size, shape and conformation of the pre-osteotomy conforming portion 21 of each fixation bone plate 20 that mounts to the non-mobile bone segment 31 is determined, along with the proper location for screw-receiving apertures 23. Likewise, the proper size, shape and conformation of the post-osteotomy conforming portion 22 of each fixation bone plate 20 that mounts to the mobile bone segment 32 is determined, along with the proper location for screw-receiving apertures 23. Furthermore, the proper size, shape and conformation of each removable pre-osteotomy alignment plate 11 that conforms to the non-mobile bone segment 31 is determined, and the proper size, shape and conformation of each removable post-osteotomy alignment plate 22 that conform is to the mobile bone segment 32 is determined. The pre-osteotomy and post-osteotomy conforming alignment plates 11/12 are connected to the one or more fixation bone plates 20 by bridging members 14 which are sized and configured to be easily severed. If present, the position and configuration of the cutting guide 13 is also determined, with the cutting guide 13 being likewise connected to the fixation bone plates 20 by bridging members 14 that are easily severed. The actual implant assembly 10 is then manufactured based on the design specifications.

Figure 2:
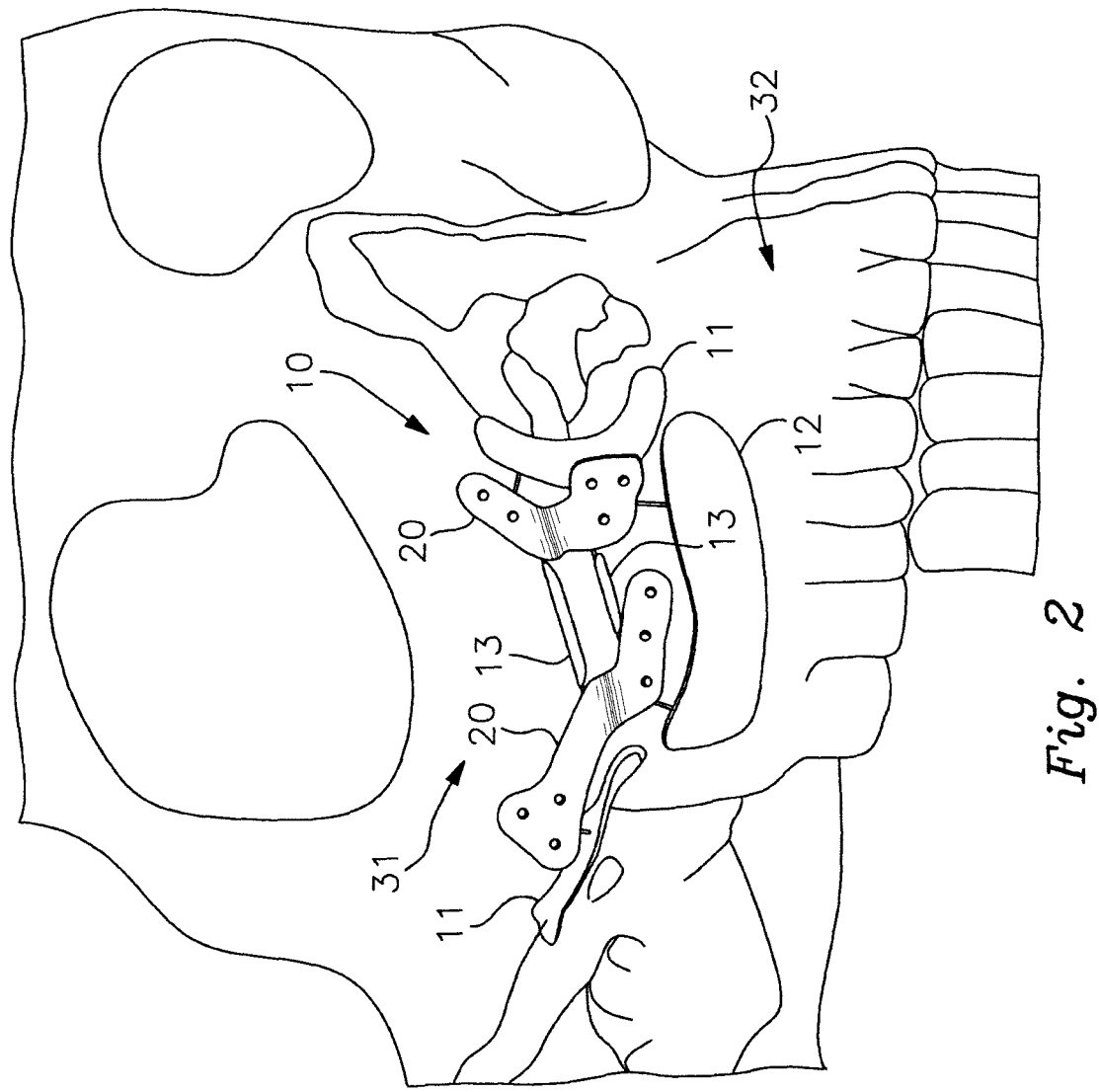
FIG. 2 illustrates the implant assembly as properly positioned on the maxilla utilizing the pre-osteotomy conforming portions of the fixation bone plates in combination with the pre-osteotomy alignment members.
Figure 4:
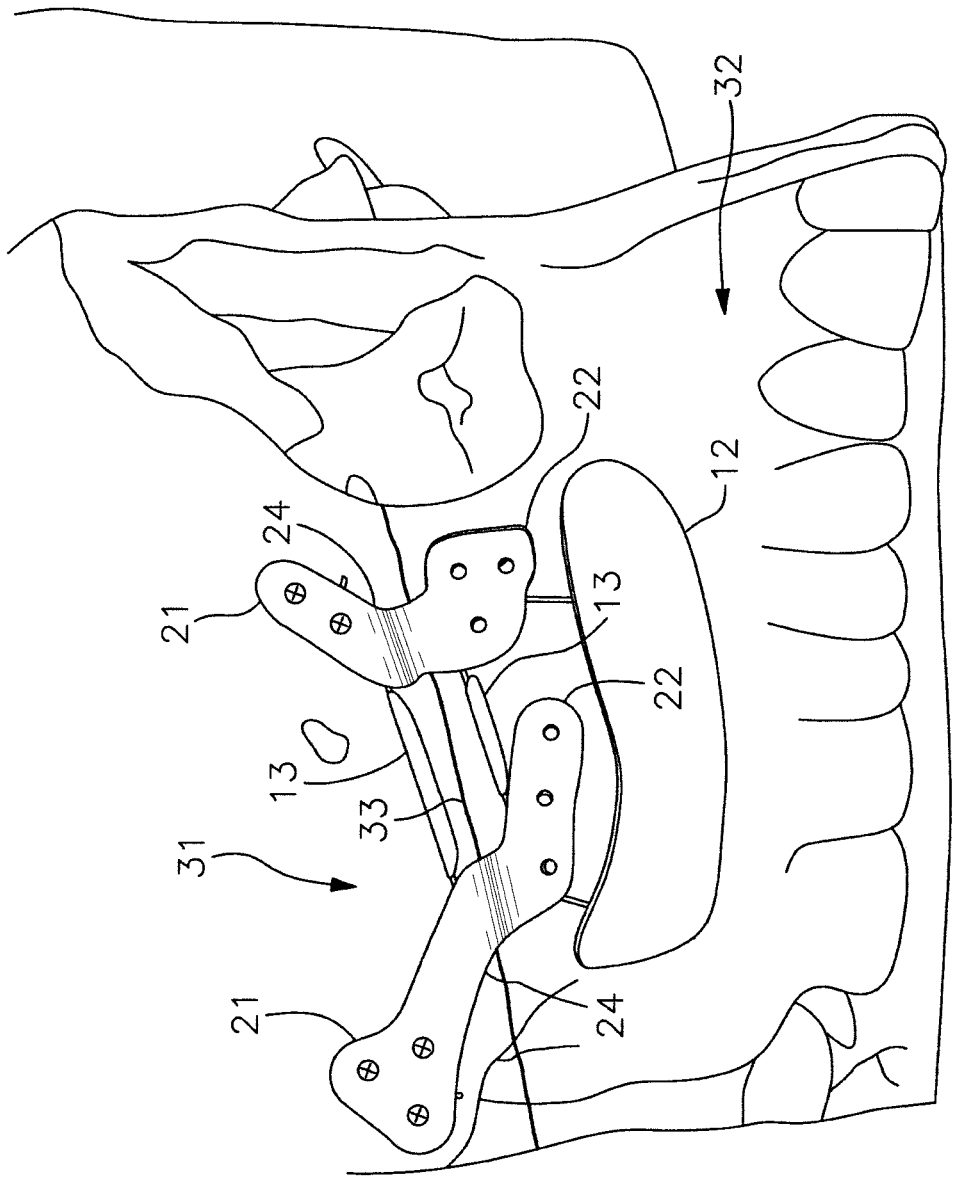
FIG. 4 illustrates the osteotomy having been performed between the cutting guide members to create the mobile bone segment.
Figure 5:
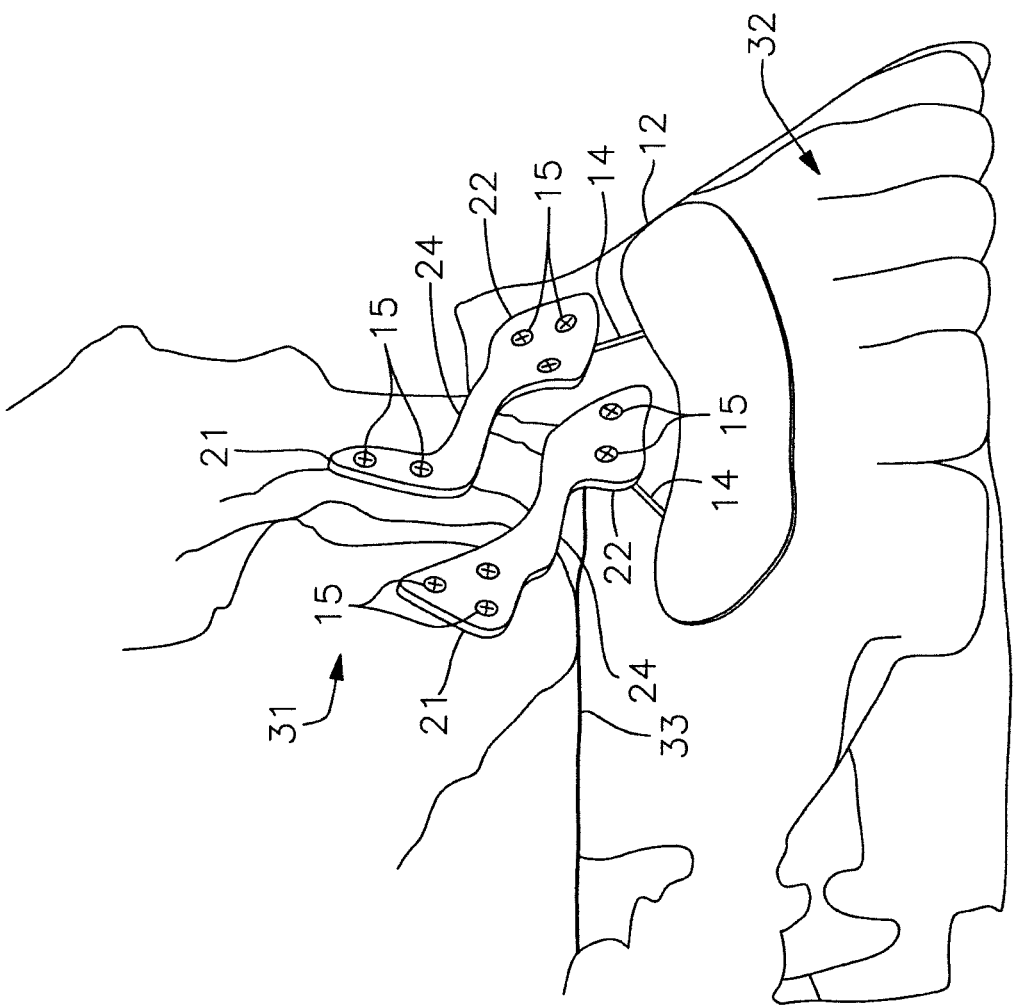
FIG. 5 illustrates the mobile bone segment repositioned relative to the non-mobile bone segment and affixed with bone screws to the post-osteotomy conforming portions of the fixation bone plates, the configuration of the post-osteotomy conforming portions of the fixation bone plates in combination with the post-osteotomy alignment member insuring proper repositioning of the mobile bone segment relative to the non-mobile bone segment.
Figure 6:
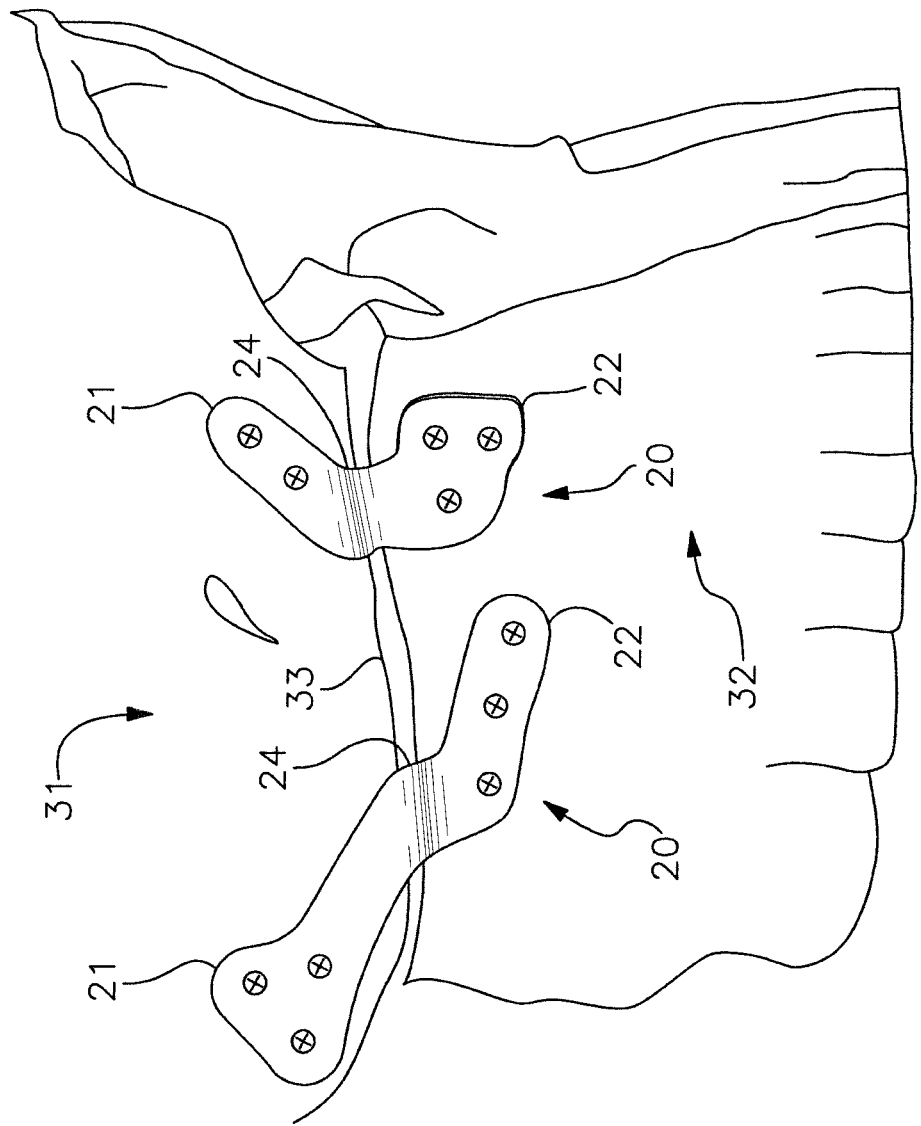
FIG. 6 illustrates the post-operative alignment member and cutting guide having been removed from the assembly.

The orthognathic procedure is accomplished by properly orienting and positioning the one or more pre-osteotomy conforming alignment plates 11 and the pre-osteotomy conforming portion 21 of the one or more fixation bone plates 20 onto the non-mobile or base bone segment 31, as shown in FIG. 2. The pre-osteotomy conforming portion 21 of each of the one or more fixation bone plates 20 is then affixed to the non-mobile bone segment 31 using bone screws or similar mechanical fasteners 15, the one or more removable pre-osteotomy conforming alignment plates 11 in combination with the pre-osteotomy conforming portions 21 of the fixation bone plates 20 insuring that the one or more fixation bone plates 20 are properly located on the non-mobile bone segment 31. The one or more removable pre-osteotomy conforming alignment plates 11 are then separated from the pre-osteotomy portion 21 of the fixation bone plates 20 by severing the bridging members 14, as shown in FIG. 3. The cutting guide 13 if present is then used to mark or perform the osteotomy 33, creating a mobile bone segment 32 detached from the non-mobile bone segment 31, as shown in FIG. 4. The cutting guide 13 is removed from the fixation bone plates 20 by severing the bridging members 14. The mobile bone segment 32 is then affixed to the post-osteotomy conforming portion 22 of the one or more fixation bone plates 20 with bone screws or similar mechanical fasteners 15, the one or more removable post-osteotomy conforming alignment plates 12 in combination with the post-osteotomy conforming portions 22 of the fixation bone plates 20 insuring that the post-osteotomy conforming portion 22 is properly located on the mobile bone segment 32, which insures that the mobile bone segment 32 is properly oriented and located relative to the non-mobile bone segment 31 in a fixed, rigid manner, as shown in FIG. 5. The one or more removable post-osteotomy conforming alignment plates 12 are then separated from the post-osteotomy conforming portion 22 of the one or more fixation bone implants 20 by severing the bridging members 14, as shown in FIG. 6. The size, shape and configuration of the transition portion 24 of each fixation bone plate 20 results in proper re-positioning of the mobile bone segment 32 relative to the non-mobile bone segment 31, such that upon bone regeneration the combined mobile and non-mobile bone segments 31/32 produce a bone structure having the desired post-operative configuration and morphology.

As previously stated, the invention applies to correction of deformities in the maxilla, mandible and chin. The figures illustrate one embodiment of the implant assembly 10 and methodology of the invention, which in this example is maxilla implant assembly 10 used in reshaping a maxilla. The figures illustrate a single implant assembly 10, and it is to be understand that a companion or second implant assembly 10 would be provided for the opposite side of the maxilla and a second osteotomy 33 would be performed in order to detach the anterior portion of the maxilla as the mobile bone segment 32.

Thus in this example the invention is an implant assembly 10 used in computer-aided orthognathic surgery for properly repositioning a mobile bone segment 32 separated by osteotomy 33 from a malformed maxilla, the implant assembly 10 comprising bone fixation apertures 23 to receive bone screws 15 positioned in the pre-osteotomy conforming portion 21 of the fixation bone plates 20, two removable pre-osteotomy alignment plate members 11 connected by bridging members 14 to the pre-osteotomy conforming portion 21 for proper pre-osteotomy placement and affixation of the implant assembly onto the non-mobile bone segment 31 of the maxilla, bone fixation apertures 23 to receive bone screws 15 positioned in a post-osteotomy conforming portion 22 of the fixation bone plates 20, a removable post-osteotomy alignment member 12 connected by bridging members 14 to the post-osteotomy conforming portions 22 of the fixation bone plate 20 for proper positioning and affixation of the mobile bone segment 32 to the post-osteotomy conforming portion 22 of the fixation bone plates 20, and a cutting guide 13 comprising two laterally-extending bars for marking the location of the osteotomy on the maxilla or for guiding the osteotomy saw during separation of the anterior mobile bone segment 32 from the posterior non-mobile bone segment 31.

The size, shape and conformation of the implant assembly 10 is determined by 3-D computer modelling, wherein the a virtual 3-D model of the maxilla is produced, a surgeon or technician then determines the best location of an osteotomy 33 and the proper repositioning of the mobile bone segment 32, and a 3-D post-osteotomy model is then produced. Based on the 3-D models, the proper size, shape and conformation of the pre-osteotomy conforming portion 21 of the fixation bone plates 20 that mount to the non-mobile bone segment 31 of the maxilla is determined, along with the proper location for screw-receiving apertures 23. Likewise, the proper size, shape and conformation of the post-osteotomy conforming portion 22 of the fixation bone plates 20 that mount to the mobile bone segment 32 of the maxilla is determined, along with the proper location for screw-receiving apertures 23. The position and shape of the cutting guide 13 is also determined. Further, the proper size, shape and conformation of the removable pre-osteotomy conforming alignment plates 11 that mount to the non-mobile bone segment 31 of the maxilla is determined, and the proper size, shape and conformation of the removable post-osteotomy alignment plate 12 that mounts to the mobile segment 32 of the maxilla is determined. The rigid implant assembly is then manufactured, as shown in FIG. 1, and properly positioned on the maxilla as shown in FIG. 2, the removable pre-osteotomy conforming alignment plates 11 insuring that the implant assembly 10 is properly located on the non-mobile segment 31 of the maxilla.

The orthognathic procedure is accomplished by then affixing the pre-osteotomy conforming portion 21 of the fixation bone plates 20 to the non-mobile segment 31 of the maxilla using bone screws 15. The removable pre-osteotomy conforming alignment plates 11 are then separated from the pre-osteotomy conforming portions 21 of the fixation bone plates 20, as shown in FIG. 3. The cutting guide 13 is then used to perform the osteotomy 33, separating a mobile bone segment 32 from the maxilla, as shown in FIG. 4. The mobile bone segment 32 is then affixed to the post-osteotomy conforming portions 22 of the fixation bone plates 20 with bone screws 15, the removable post-osteotomy alignment plate 12 insuring that the mobile bone segment 32 is properly located on the post-osteotomy conforming portions 22 of the fixation bone plates 20, as shown in FIG. 5. The removable post-osteotomy alignment plate 12 is then separated from the post-osteotomy conforming portions 22, as shown in FIG. 6. The size, shape and configuration of the fixation bone plates 20 results in proper re-positioning of the mobile bone segment 32 relative to the non-mobile bone segment 31 of the maxilla, such that upon bone regeneration the combined mobile and non-mobile bone segments 31/32 produce a maxilla having the desired post-operative configuration.

It is understood that equivalents and substitutions for certain elements and steps set forth above may be obvious to those of skill in the art, and therefore the true scope and definition of the invention is to be as set forth in the following claims.

We claim:

1. A customized, patient-specific implant assembly configured to fixedly position a first bone segment relative to a second bone segment across an osteotomy gap, the first and second bone segments having surface topographies, the implant assembly comprising:
   one or more fixation bone plates each comprising a pre-osteotomy conforming portion and a post-osteotomy conforming portion joined by a transition portion, the transition portion of the one or more fixation bone plates configured to span the osteotomy gap;
   wherein the pre-osteotomy conforming portion is configured to conform to a portion of the first bone segment surface topography, and wherein the post-osteotomy conforming portion is configured to conform to a portion of the second bone segment surface topography;
   bone screws configured to affix the one or more fixation bone plates to bone across the osteotomy gap;
   bone screw apertures configured to receive the bone screws, the bone screw apertures disposed in the pre-osteotomy conforming portions and the post-osteotomy conforming portions of the one or more fixation bone plates;
   one or more removable pre-osteotomy conforming alignment plates connected to the pre-osteotomy conforming portions of the one or more fixation bone plates by severable bridging members; wherein the one or more removable pre-osteotomy conforming alignment plates are configured to conform to a portion of the surface topography of the first bone segment different from the portion of the first bone segment surface topology conformed to by the pre-osteotomy conforming portion of the one or more fixation bone plates;
   one or more removable post-osteotomy conforming alignment plates connected to the post-osteotomy conforming portions of the one or more fixation bone plates by severable bridging members; wherein the one or more removable post-osteotomy conforming alignment plates are configured to conform to a portion of the surface topography of the second bone segment different from the portion of the second bone segment surface topology conformed to by the post-osteotomy conforming portion of the one or more fixation bone plates;
   wherein the assembly is configured such that, with the one or more fixation plates affixed across the osteotomy gap with the bone screws, the one or more removable pre-osteotomy conforming alignment plates and the one or more removable post-osteotomy conforming alignment plates are removable from the one or more fixation plates by severing the bridging members.

2. The implant assembly of claim 1, further comprising a removable cutting guide connected to the one or more fixation bone plates.

3. The implant assembly of claim 1, wherein the pre-osteotomy conforming portion and the post-osteotomy conforming portion of each of the one or more fixation bone plates comprises a surface contact area, and wherein the one or more removable pre-osteotomy conforming alignment plates and the one or more post-osteotomy conforming alignment plates each comprise a contact surface area greater than the contact surface area of the pre-osteotomy conforming portion and the post-osteotomy conforming portion of each of the one or more fixation bone plates.

4. The implant assembly of claim 2, wherein the pre-osteotomy conforming portion and the post-osteotomy conforming portion of each of the one or more fixation bone plates comprises a surface contact area, and wherein the one or more removable pre-osteotomy conforming alignment plates and the one or more post-osteotomy conforming alignment plates each comprise a contact surface area greater than the contact surface area of the pre-osteotomy conforming portion and the post-osteotomy conforming portion of each of the one or more fixation bone plates.

5. The implant assembly of claim 1, wherein the one or more removable pre-osteotomy conforming alignment plates and the one or more post-osteotomy conforming alignment plates are non-planar.

6. The implant assembly of claim 2, wherein the one or more removable pre-osteotomy conforming alignment plates and the one or more post-osteotomy conforming alignment plates are non-planar.

7. The implant assembly of claim 3, wherein the one or more removable pre-osteotomy conforming alignment plates and the one or more post-osteotomy conforming alignment plates are non-planar.

8. A customized, patient-specific implant assembly configured to fixedly position a mobile bone segment relative to a non-mobile bone segment, the mobile and non-mobile bone segments having surface topographies, the implant assembly comprising:
   one or more fixation bone plates each comprising a pre-osteotomy conforming portion and a post-osteotomy conforming portion joined by a transition portion, wherein the pre-osteotomy conforming portion is configured to conform to a portion of the surface topography of the non-mobile bone segment, and wherein the post-osteotomy conforming portion is configured to conform to a portion of the surface topography of the mobile bone segment;
   bone screws configured to affix the one or more fixation bone plates to the bone segments;
   bone screw apertures configured to receive the bone screws, the bone screw apertures disposed in the pre-osteotomy conforming portions and the post-osteotomy conforming portions of the one or more fixation bone plates;
   one or more removable pre-osteotomy conforming alignment plates connected to the pre-osteotomy conforming portions of the one or more fixation bone plates by severable bridging members; and
   one or more removable post-osteotomy conforming alignment plates connected to the post-osteotomy conforming portions of the one or more fixation bone plates by severable bridging members,
   wherein the one or more removable pre-osteotomy conforming alignment plates are configured to conform to other portions of the surface topography of the non-mobile bone segment, and wherein the one or more removable post-osteotomy conforming alignment plates are configured to conform to other portions of the surface topography of the mobile bone segment;

wherein the assembly is configured such that, with the one or more fixation plates affixed to the bone segments by the bone screws, the one or more removable pre-osteotomy conforming alignment plates and the one or more removable post-osteotomy conforming alignment plates are removable from the one or more fixation plates by severing the bridging members.

9. The implant assembly of claim 8, further comprising a removable cutting guide connected to the one or more fixation bone plates.

10. The implant assembly of claim 8, wherein the pre-osteotomy conforming portion and the post-osteotomy conforming portion of each of the one or more fixation bone plates comprises a surface contact area, and wherein the one or more removable pre-osteotomy conforming alignment plates and the one or more post-osteotomy conforming alignment plates each comprise a contact surface area greater than the contact surface area of the pre-osteotomy conforming portion and the post-osteotomy conforming portion of each of the one or more fixation bone plates.

11. The implant assembly of claim 9, wherein the pre-osteotomy conforming portion and the post-osteotomy conforming portion of each of the one or more fixation bone plates comprises a surface contact area, and wherein the one or more removable pre-osteotomy conforming alignment plates and the one or more post-osteotomy conforming alignment plates each comprise a contact surface area greater than the contact surface area of the pre-osteotomy conforming portion and the post-osteotomy conforming portion of each of the one or more fixation bone plates.

\* \* \* \* \*